United States Patent
Lange et al.

(10) Patent No.: US 6,725,704 B2
(45) Date of Patent: Apr. 27, 2004

(54) GAS ANALYZER

(75) Inventors: Jesper Lange, Ballerup (DK); Jorgen Christensen, Snekkersten (DK)

(73) Assignee: PAS Technology A/S, Birkerod (DK)

( * ) Notice: Subject to any disclaimer, the term of this patent is extended or adjusted under 35 U.S.C. 154(b) by 0 days.

(21) Appl. No.: 10/148,944

(22) PCT Filed: Jan. 12, 2001

(86) PCT No.: PCT/DK01/00021
§ 371 (c)(1),
(2), (4) Date: Jun. 6, 2002

(87) PCT Pub. No.: WO01/51916
PCT Pub. Date: Jul. 19, 2001

(65) Prior Publication Data
US 2002/0178782 A1 Dec. 5, 2002

(30) Foreign Application Priority Data
Jan. 14, 2000 (DK) .................................. 2000 00056

(51) Int. Cl.[7] ............................................... G01N 19/10
(52) U.S. Cl. ...................... 73/23.2; 73/23.24; 73/23.25
(58) Field of Search ................ 73/23.2, 24.01, 73/23.24, 23.25, 31.04, 23.37; 250/336

(56) References Cited
U.S. PATENT DOCUMENTS

| | | | | |
|---|---|---|---|---|
| 3,748,594 A | * | 7/1973 | Pugh | 372/58 |
| 3,860,818 A | * | 1/1975 | Stalder et al. | 250/343 |
| 4,055,764 A | * | 10/1977 | Dimeff | 250/336.1 |
| 4,818,882 A | | 4/1989 | Nexo et al. | 250/343 |
| 5,616,826 A | * | 4/1997 | Pellaux et al. | 73/24.02 |
| 5,753,797 A | * | 5/1998 | Forster et al. | 73/24.01 |

* cited by examiner

Primary Examiner—Hezron Williams
Assistant Examiner—Katina Wilson
(74) Attorney, Agent, or Firm—Cooper & Dunham LLP; Donald S. Dowden

(57) ABSTRACT

A gas analyzer has a measuring chamber, a gas inlet channel, a gas outlet channel, a pump for providing a gas flow through the chamber, a device for irradiating the gas in the chamber with pulsating electromagnetic energy to generate acoustic pressure fluctuations therein, and at least one microphone communicating with the chamber for detecting the fluctuations. The inlet channel and the outlet channel each has an acoustic filter formed by channels with reduced sectional area of flow and a plurality of cavities associated therewith. The gas analyzer has at least one sandwich device formed of joined plate-like elements. The channel sections of the inlet and/or outlet channel are defined by at least two elements and the vibration-reducing cavities are also defined by at least two elements. The connections between the respective channels and cavities are formed as transverse apertures in the elements or element portions adjoining the channel and the cavities, respectively.

11 Claims, 6 Drawing Sheets

GAS ANALYZER

TECHNICAL FIELD

The invention relates to a gas analyser comprising a measuring chamber, a gas inlet channel for supplying gas to the measuring chamber, a gas outlet channel for removing gas from the measuring chamber, means for providing a predetermined volume flow rate through the measuring chamber, a device for affecting the gas in the measuring chamber with pulsating magnetic or electromagnetic energy of predetermined pulse rates so as to generate acoustic pressure fluctuations therein, the inlet channel and the outlet channel each comprising an acoustic filter in form of channel sections with reduced sectional area of flow so as to provide a predetermined flow resistance, and a plurality of cavities of a predetermined volume associated therewith.

BACKGROUND ART

The gas analyser of the above type may either be formed as a so-called paramagnetic gas analyser employed for measuring the oxygen content in a gas or as a so-called photoacoustic gas analyser, which hereinafter is denoted as PGA (photoacoustic gas analyser), employed for measuring the incidence of one or more specific gasses in a gas mixture.

In a paramagnetic electromagnetic gas analyser the affecting device is an electromagnet affecting the gas in the chamber with a pulsating magnetic field. As oxygen in practice is the only occurring gas, which is paramagnetic, the pulsating magnetic field generates pressure changes in the gas in the measuring chamber depending on the oxygen portion in the gas. These pressure changes are detected by means of a microphone.

In a photoacoustic gas analyser is the affecting device is an electromagnetic radiation source affecting the gas in the measuring chamber with electromagnetic radiation, eg. infrared light. The energy from the light source is periodically absorbed by gas mixture and causes a periodic heating resulting in a corresponding increase in the pressure of the gas. The gas is cooled between the light pulses, whereby the pressure in the chamber decreases correspondingly. These pressure changes are detected by means of a microphone connected to the chamber. Due to the composition of the individual gas mixture constituents the absorption wavelength thereof differs from one another. If the wavelength of the modulated light is set to be close to one of these absorption wavelengths, the rise in temperature and thus the pressure in the chamber increases as the portion of the gas constituent having the absorption wavelength in question increases.

Both in a paramagnetic and in a photoacoustic gas analyser the accuracy of the measurement is conditional on the measuring chamber being kept closed during the measuring process in the sense that the produced pressure fluctuations are retained in the chamber and external noise is prevented from entering the chamber. For instance in connection with a photoacoustic gas analysis this may be obtained by allowing a measured amount of gas to enter the measuring chamber prior to a measurement and subsequently closing off the measuring chamber during the measurement per se.

This measuring method is known from U.S. Pat. No. 4,818,882 and used in the device entitled Multi-gas Monitor, type 1302, from the company of Innova Air Tech Instruments. The said measuring method is, however, encumbered by the drawback that the measurement is intermittent and the measuring time is relatively long, typically of 30–60 seconds. As some physiological measurements require a response time of typically 0.1 second, this measuring method is unsuitable for such applications. Another measuring method is to employ so-called acoustic filters to prevent noise from reaching the measuring chamber and affecting the measuring results—at least in the frequency area corresponding to the photoacoustic frequencies. Such acoustic filters allow for a constant volume flow rate through the measuring chamber and is described in the above U.S. Pat. No. 4,818,882.

The said acoustic filters may be formed of narrow flow channels or restrictions providing resistance to gas flow therethrough and of cavities communicating therewith attenuating pressure changes in the gas flow. In order to facilitate the calculation of acoustic filters, the restrictions and the cavities can be equivalent to the electric resistances and capacities, respectively, as the differential equations used for the two systems also are equivalent. Pressure and volume flow rate thus correspond to electric voltage and current, respectively. The cavities may communicate with the flow channels such that the gas flows through said cavities. If, however, a quick response time is required, it is advantageous in relation to the inlet channel to connect the cavities to the flow channel via lateral branches such that the inflowing gas does not flow through the cavities and thereby is mixed with the gas therein.

The number and size of the restrictions and the cavities is determined by the desired physical size of the system and of the frequencies to be dampened by the acoustic filter. Long, thin restrictions offer more resistance to flow than short, wide restrictions and large cavities dampen lower frequencies than small cavities. For obtaining sufficient damping, an acoustic filter may comprise several successive parts formed of a restriction and a cavity, respectively.

The device known as Anaesthetic Gas Monitor Type 1304 from the company of Innova Air Tech Instruments, discloses a PGA comprising acoustic filters of the above type, in which the restrictions of the acoustic filters are formed of thin needle tubes and each cavity of a metal container with a hose connector communicating with the cavity of the container. The needle tubes and the container connectors are interconnected by means of a short silicone hose. One drawback of such a structure is that it is relatively sensitive to vibrations. Yet another drawback is that the structure comprises a large number of components resulting in an expensive and time-consuming manufacture and assembling thereof. Furthermore, in needle tubes with a circular inner cross section, the flow resistance is inversely proportional to the radius in the fourth power. Consequently deviations from the nominal radius result in a quadruple relative deviation of the flow resistance from the nominal value thereof.

A need thus exists for a gas analyser with acoustic filters, which is less sensitive to vibrations and which is more simple to manufacture than the known gas analysers.

BRIEF DESCRIPTION OF THE INVENTION

The gas analyser according to the invention is characterised in that it comprises at least one sandwich device formed of joined plate-like elements, the channel sections with reduced flow area of the inlet channel and/or the outlet channel being defined by at least two elements and the cavities also being defined by at least two elements, the connections between the respective channel and the respective cavities being provided as transverse apertures in the elements or element portions adjoining the channel and the cavities, respectively.

Since the sandwich device is a mechanically rigid structure, which is insensitive to vibrations, a photoacoustic gas analyser, which is less sensitive to vibrations than known gas analysers, is obtained. Furthermore it is comparatively simple to manufacture and assemble the relatively few elements of the sandwich device. In addition to the acoustic filter it is, moreover, also possible to incorporate other flow channels of the analyser into the sandwich device. The sandwich device thus enables the provision of a very compact gas analyser. Furthermore the fundamental structure of the sandwich device, wherein flow channels are arranged at different levels, is comparable with the structure of printed circuit boards.

According to a preferred embodiment of the invention, the acoustic filters of the inlet channel and the outlet channel may be provided in the same sandwich device so as to obtain a simple and compact embodiment.

Moreover according to the invention the channel or channels of the sandwich device may be defined by a non-through-going groove in a first element and an adjoining second element, in which the transverse apertures connecting the channel with the cavities is formed.

Furthermore according to the invention the channel or channels of the sandwich device may be defined by a through-going slit in a first element and two further adjacent elements, one provided on either side of the first element, the transverse apertures connecting the channel with the cavities being formed in one of the further elements.

According to a preferred embodiment of the invention the first element may be formed of a metal foil having a thickness of between 0.05 and 0.5 mm, preferably 0.1 and 0.2 mm, the width of the slit exceeding the foil thickness, preferably by at least two to three times. As the metal foil thus preferably is rather thin compared to the width of the slit, the width of the channel somewhat exceeds its height, whereby a deviation from the nominal height of the channel only results in the triple deviation of the flow resistance from its nominal value. Since metal foils of very accurate thickness tolerances are readily available, it is expected that a higher degree of accuracy of the flow resistance may be obtained by use thereof than by use of needle tubes. The slits in the metal foils are formed in an accurate processing method, preferably an etching method, so as to prevent burrs on the element in question.

Furthermore according to the invention the transverse apertures may be formed in the same element as the cavities, the cavities being defined by a separate plate-like element on the side opposite the transverse apertures.

Moreover according to the invention the cavities may be formed as recesses in a separate element abutting the elements comprising the transverse apertures.

Furthermore according to the invention each of the cavities associated with the acoustic filter of the inlet channel may communicate with the acoustic filter of the outlet channel via a shunt channel. The shunt channel provides a minor partial flow through the cavities associated with the acoustic filter of the inlet channel and bypassed of the measuring chamber to ensure that a gas interchange between the gas in the inlet channel and the gas in the associated cavities is not effected. Such a gas interchange would have an adverse effect on the response time and the measuring accuracy. The shunt channel is typically dimensioned such that the volume flow rate therethrough is in the order one tenth of the volume flow rate through the measuring chamber.

Furthermore according to the invention the shunt channel may be provided partly by means of at least two plate-like elements of the sandwich device defining shunt channel sections, said elements preferably differing from the elements defining the inlet channel, the outlet channel and the cavities, respectively, and partly by transverse apertures connecting the shunt channel sections with the cavities in the acoustic filter of the inlet channel and with the acoustic filter of the outlet channel, respectively.

Finally according to the invention substantially all of the flow channels of the gas analyser may be provided in elements of the sandwich device. As a result a very compact and rigid structure is obtained which is insensitive to vibrations.

BRIEF DESCRIPTION OF THE DRAWINGS

The invention is explained in detail below with reference to the drawings, in which.

BEST MODE FOR CARRYING OUT THE INVENTION

Figure 1:
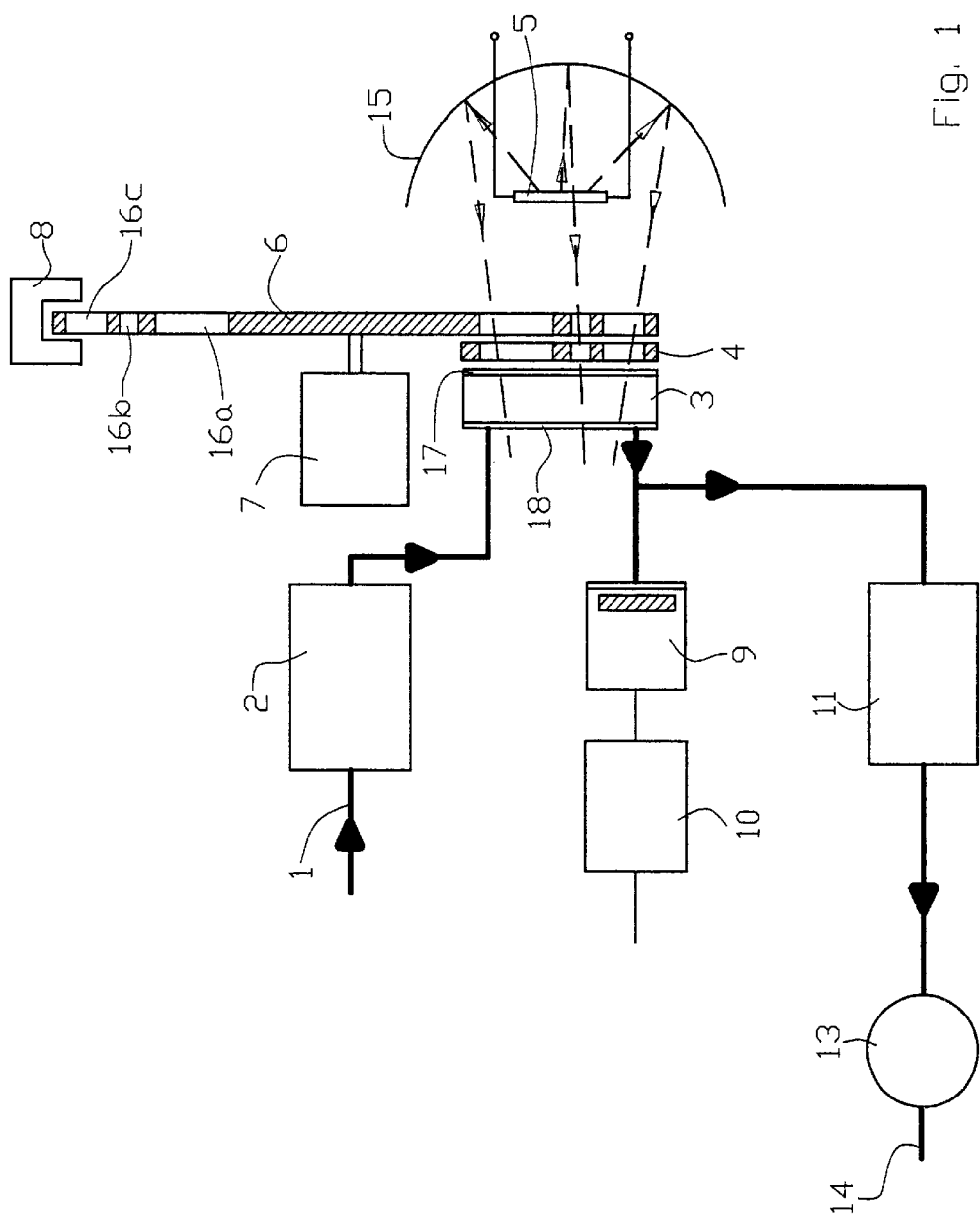
FIG. 1 is a flow chart of a photoacoustic gas analyser according to the invention.

The photoacoustic gas analyzer shown in FIG. 1 comprises a gas inlet channel 1 provided with a first acoustic filter 2 and through which the gas to be analysed is passed to inlet of a photoacoustic measuring chamber 3. Light is emitted towards the measuring chamber 3 by means of an infrared light source 5 (other types of electromagnetic radiation may also be used) and a reflector 15. Before reaching the measuring chamber the light passes a so-called chopper wheel 6 comprising at least one—and in the present case three—concentric rows of apertures 16a, 16b and 16c. The apertures in each row are of the same size and mutually evenly interspaced, while the number of apertures in the rows differs from each other corresponding to the different modulating frequencies. The wheel is made to rotate about its centre by means of a motor 7, whose rotational speed is controlled by means of an optical tachometer 8. The chopper wheel 6 generates the pulsating electromagnetic radiation necessary for generating measurable pressure fluctuations in the gas constituents to be detected in the measuring chamber 3 by means of the gas analyzer. The electromagnetic radiation pulsed by the chopper wheel 6 then passes a number of optical filters 4 corresponding to the number of rows of apertures. Each of the optical filters selects a specific wavelength of the infrared light corresponding to the absorption bands of each of the gasses to the measured. Then the light passes through a first window 17, which is transparent to infrared light, and into the measuring chamber and having passed therethrough the light exits through another window 18, which also is transparent to infrared light. The measuring chamber 3 further communicates with a gas outlet channel 14 provided with a pump 13. A second acoustic filter 11 is provided in the gas outlet channel 14 between the pump 13 and the measuring chamber 3. A measuring microphone 9 communicates with the gas outlet channel 14 between the measuring chamber 3 and the second acoustic filter 11, said microphone 9 detecting the acoustic signals generated in the measuring chamber 3 and converting these into an electric signal amplified by a microphone amplifier 10 for further signal processing.

Figure 2:
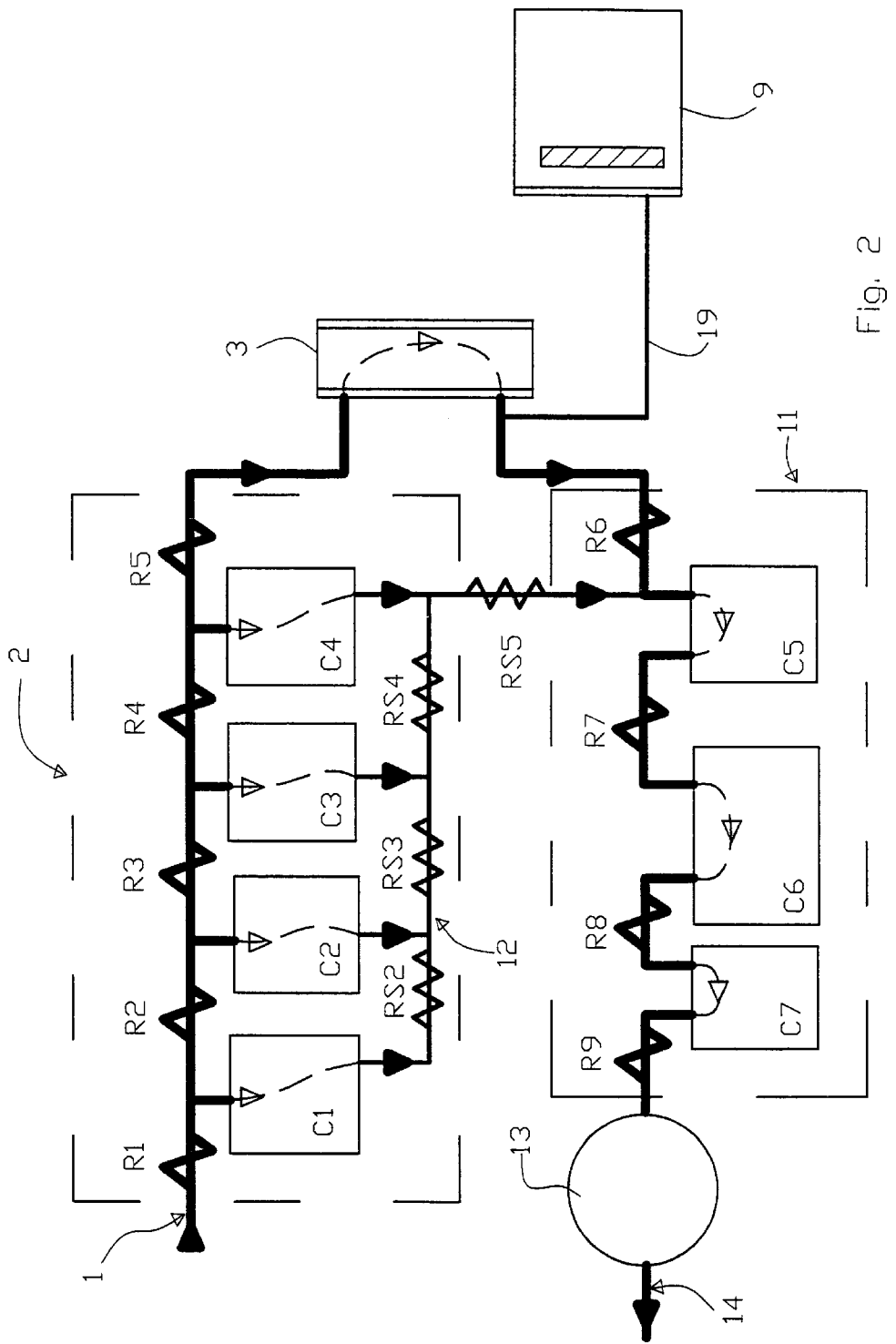
FIG. 2 is a chart of the gas flow in the gas analyser.

The gas flows in the photoacoustic gas analyser in FIG. 1 and in particular the structure of the first filter 2 and the second filter 11 associated with the inlet channel 1 and the outlet channel 14, respectively, is shown in FIG. 2. The first acoustic filter 2 comprises a number of inlet channel sections with reduced sectional area of flow or restrictions R1,R2, R3,R4,R5 and a plurality of cavities C1,C2,C3 and C4 communicating with separate lateral branches between the restrictions for obtaining a fast response time. The second acoustic filter 11 of the gas outlet channel 14 similarly comprises a number of channel sections with reduced flow area or restrictions R6,R7,R8 and R9 and cavities C5,C6 and C7 connected therewith. The restrictions R6 to R9 of the outlet channel communicate with the cavities C5 to C7 such that a gas flow through the cavities is provided. This rather simple embodiment of the acoustic filter may be used in the outlet channel 14 without adversely affecting the response time.

By means of a shunt channel 12 comprising channel sections with reduced flow area or restrictions RS2, RS3, RS4 and RS5 each of the cavities C1, C2, C3 and C4 communicates with the outlet channel 14 in the area at the cavity C5 thereof. The shunt channel 12 serves to provide a shunt flow through the cavities C1 to C4 and bypassed of the measuring chamber 3. This shunt flow prevents a gas interchange between the gas in the cavities C1–C4 and the gas flow in the inlet channel 1 and thus improves the response time and the accuracy of measurement. Finally it appears from FIG. 2 that the microphone 9 communicates with the outlet channel 14 immediately downstream of the measuring chamber 3 by means of a microphone channel 19. It should be noted that the microphone 9 of course may communicate directly with the measuring chamber 3 via a separate channel.

Figure 3:
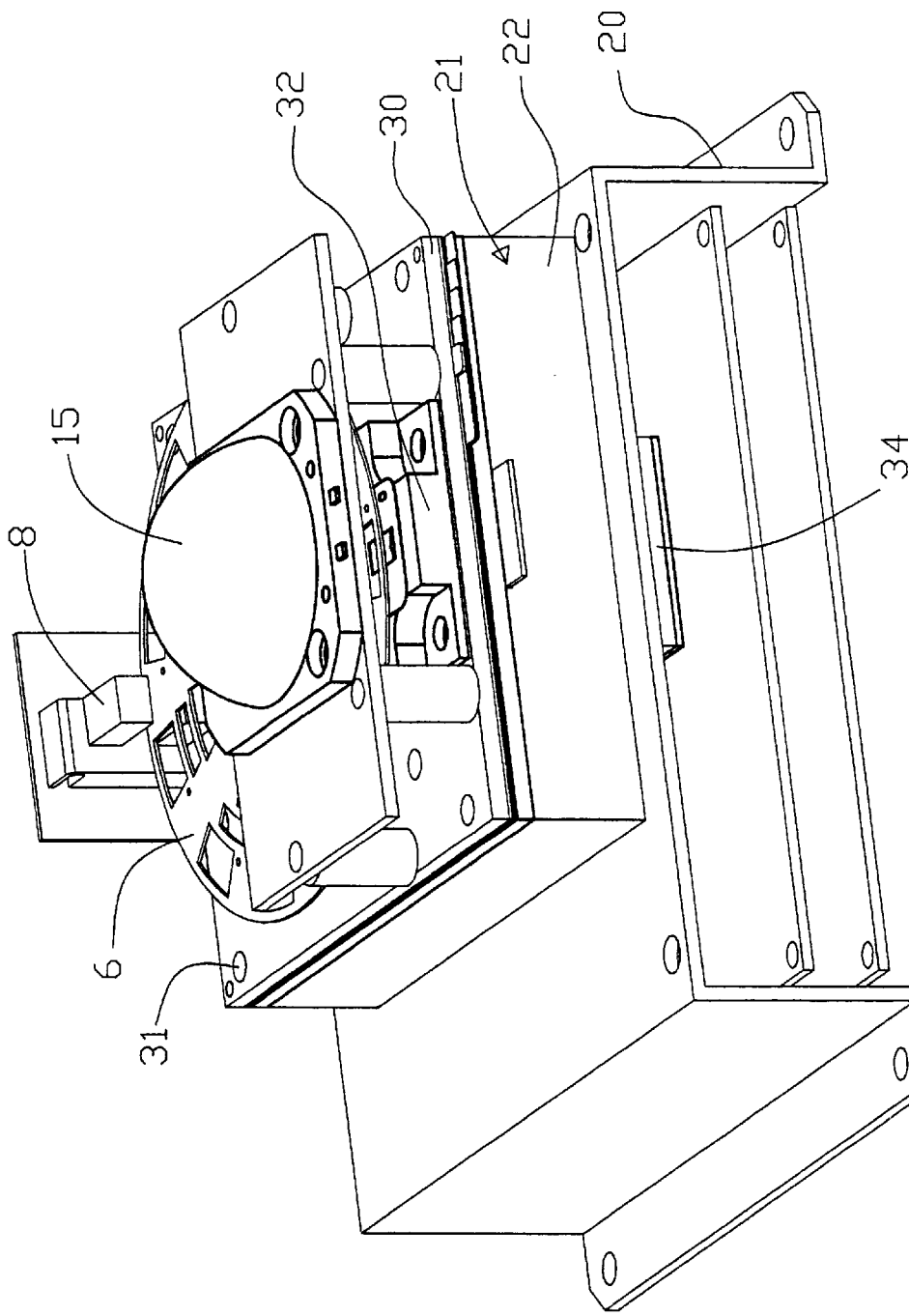
FIG. 3 is a perspective illustration of a preferred embodiment of a gas analyser according to the invention.
Figure 4:
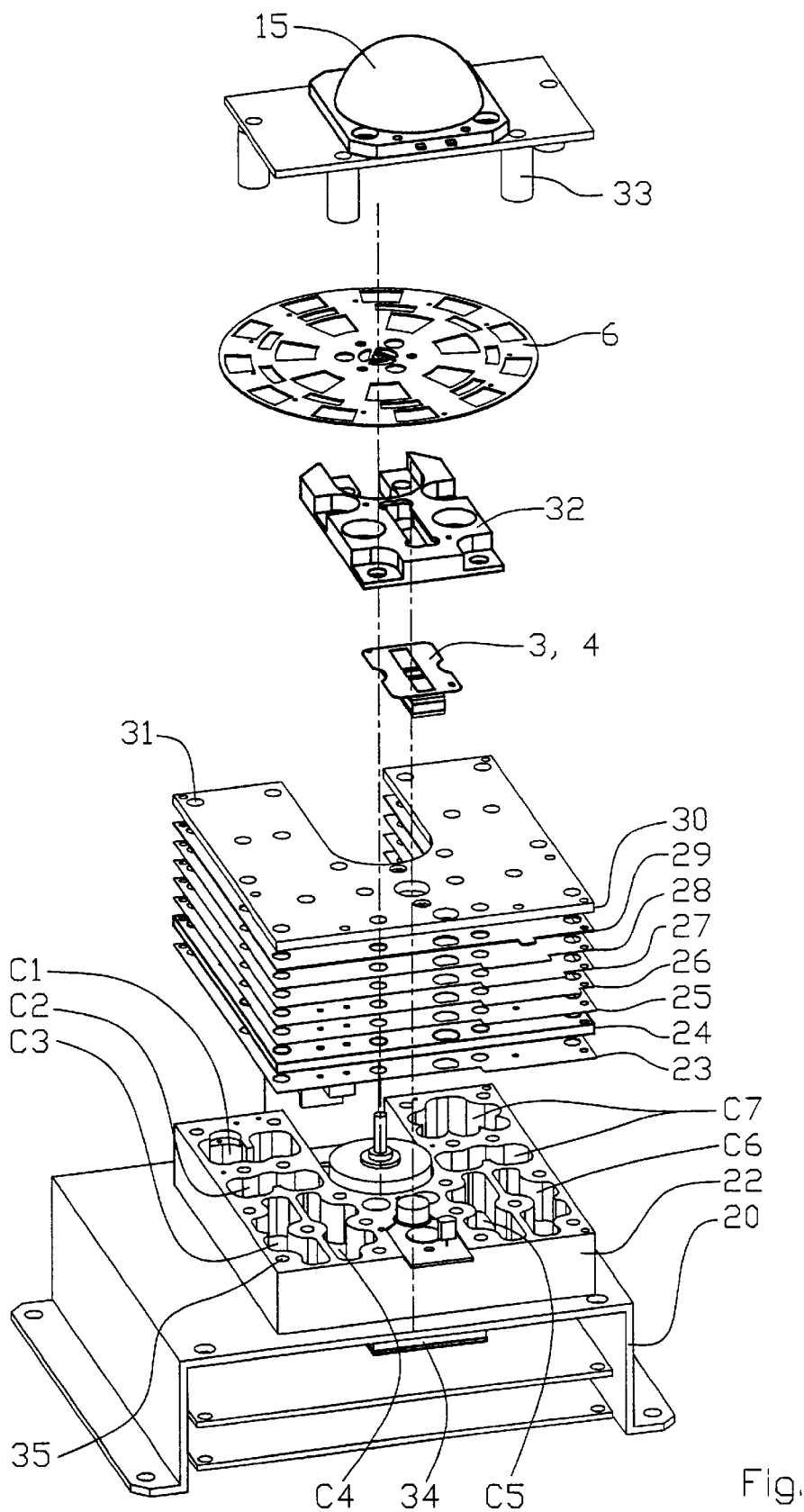
FIG. 4 is an exploded view of the gas analyser shown in FIG. 3.

FIGS. 3 and 4 show a preferred embodiment of a gas analyser according to the invention comprising a frame 20, on which a sandwich device 21 is arranged comprising a plurality of superposed and joined plate-shaped elements 22–30 for providing the flow channels and acoustic filters of the gas analyser. When seen in direction from the frame 20, the sandwich device 21 comprises a block 22 in which the cavities C1–C7 are provided in form of recesses. A gasket 23 is sandwiched between the block 22 and a lower plate 24, said plate upwardly defining the cavities and being provided with transverse apertures for connecting the respective cavities with a superposed main channel foil 25. The main channel foil 25 is provided with through-going slits so as to form inter alia the inlet channel 1 and the outlet channel 14. Downwardly, the lower plate 24 defines the slits in the main channel foil 25, while the slits are upwardly defined by a separation foil 26. The separation foil 26 is provided with through-going apertures to provide the necessary flow connections between the plate-shaped element arranged thereunder and a shunt channel foil 27 arranged thereabove and defining the shunt channel 12. The slit formed in the shunt channel foil is downwardly defined by the separation foil 26 and upwardly defined by a cover foil 28 so as to form the shunt channel 12. A cover plate 30 is arranged above the cover foil 28, a pressure-distributing gasket 29 being arranged therebetween. The plate-shaped elements 23–29 arranged between the cover plate 30 and the block 22 are bolted together between the block and the cover plate by means of bolts (not shown), said bolts extending through apertures 31 in the elements and screwed into threaded holes 35 in the block 22.

As regards the sandwich device 21 it should be noted that the gaskets 23 and 29 optionally may be omitted and that the cavities and the restriction thereof may be provided in manner differing from the manner described above. By omitting the gasket it is thus possible also to form the lower plate 24 integrally with the block. The cavities are then provided by means of recesses in the lower face of the block and downwardly defined by a separate plate-shaped element.

A housing 32 is mounted on the cover plate 30 as retainer for the measuring chamber 3 and the optical filters 4. The motor 7 for driving the chopper wheel 6 is attached to the frame 20 in the space between the legs of the sandwich device 21, which is U-shaped in a top view. The infrared light source 5 with associated reflector 15 is arranged in a support 33 attached to the cover plate 30. The microphone 9 (not shown in FIGS. 3 and 4) is arranged in a microphone housing 34 received in a recess on the lower face of the block. Finally it should be noted that the inlet opening 38 of the gas inlet channel 1 and the outlet opening 37 of the gas outlet channel 14 (confer FIGS. 5 and 6) are formed of through-going apertures in the bottom of the block and that a pump corresponding to the pump 13 in FIGS. 1 and 2 is connected to the outlet of the gas outlet channel.

Figure 5:
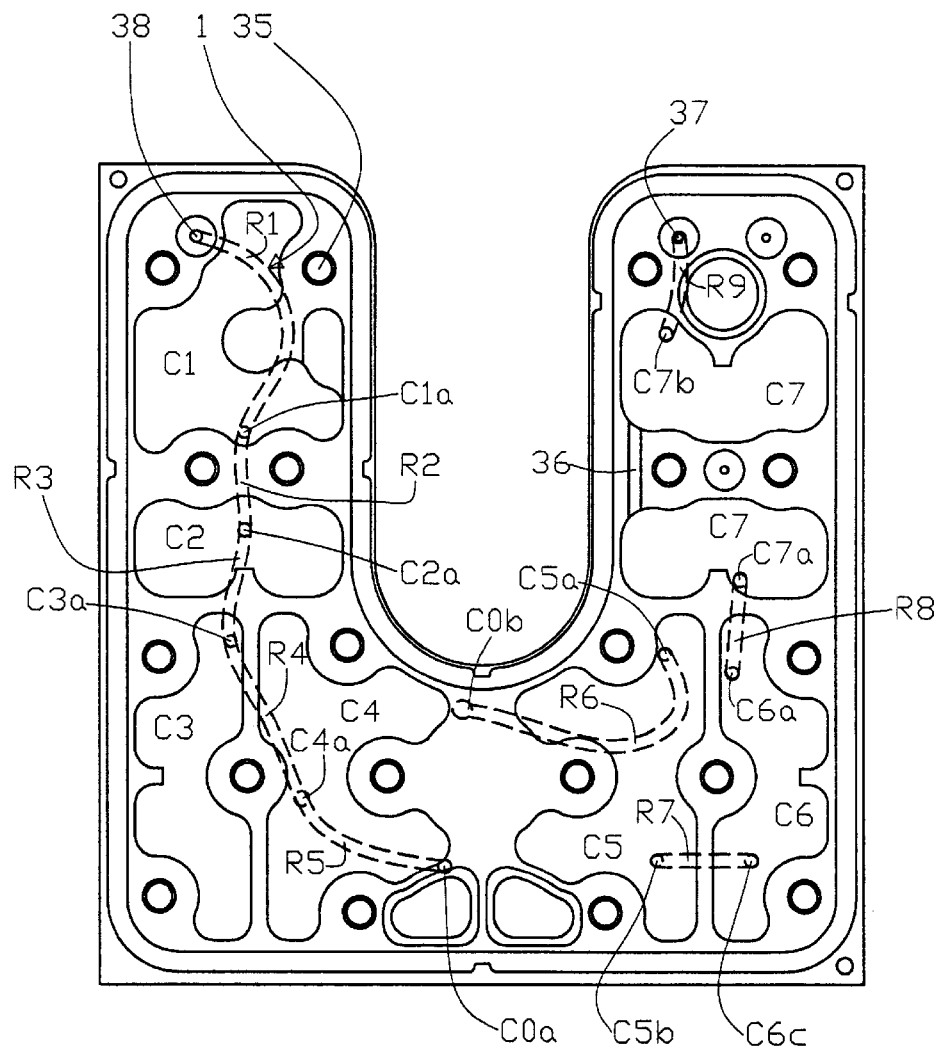
FIG. 5 illustrates plate-shaped elements forming part of the sandwich device of the gas analyser shown in FIGS. 3 and 4, said elements forming the acoustic filters of the inlet and outlet channels.

The structure of the sandwich device 21 is described in detail below with reference to FIGS. 5 and 6. FIG. 5 is a top view of the block 22, the cavities C1–C7 formed therein shown by means of solid lines. The through-going slits formed in the main channel foil 25 are shown by means of dotted line, said slits defining the inlet channel 1 and the outlet channel 14 with the associated restrictions R1–R5 and R6–R9, respectively. Furthermore the through-going apertures in the lower plate 24 are illustrated by means of dotted circles, said apertures connecting the cavities with the channels. It should furthermore be noted that the same reference numerals as used in FIG. 2 have been used for the cavities and the restrictions of the channels. The gas to be analysed flows from below into the block through the inlet 38 and thus enters the inlet channel 1, which is defined by the slit in the main channel foil 25 and the lower plate 24 and the separation foil 26 arranged on either side of the main channel foil 25. The inlet channel comprises the restrictions R1,R2,R3,R4 and R5. The inlet channel 1 communicates with the chamber C1 between the restrictions R1 and R2 via the aperture C1a in the lower plate 24. In a corresponding manner between the restrictions R2 and R3 the inlet channel 1 communicates with the cavity C2 via the aperture C2a in the lower plate 24, between the restrictions R3 and R4 the channel communicates with the cavity C3 via the aperture C3a and between the restrictions R4 and R5 the channel communicates with the cavity C4 via the aperture C4a. The restriction R5 communicates with an aperture C0a communicating with the inlet to the measuring chamber 3 in a manner not shown in detail. Correspondingly the outlet of the measuring chamber 3 communicates with the aperture C0b in a manner not shown in detail, said aperture communicating with the restriction R6 of the outlet channel 14. As the further restrictions R7, R8 and R9 of the outlet channel, R6 is formed as a through-going slit in the main channel foil 25. The restriction R6 communicates with the cavity C5 via a through-going aperture C5a in the lower plate 24. Furthermore the cavities C5 and C6 are interconnected by means of the restriction R7 and the apertures C5b and C6c in the lower plate 24. In a corresponding manner the cavity C6 communicates with the cavity C7 via the restriction R8 and the apertures C6a and C7a in the lower plate 24. The cavity C7 is formed of two cavity halves interconnected by means of a channel 36 in the block 22 and the cavity C7 communicates with the outlet 37 of the block via the restriction R9 and an aperture C7b and an aperture arranged in the lower plate 24 above the outlet 37.

Figure 6:
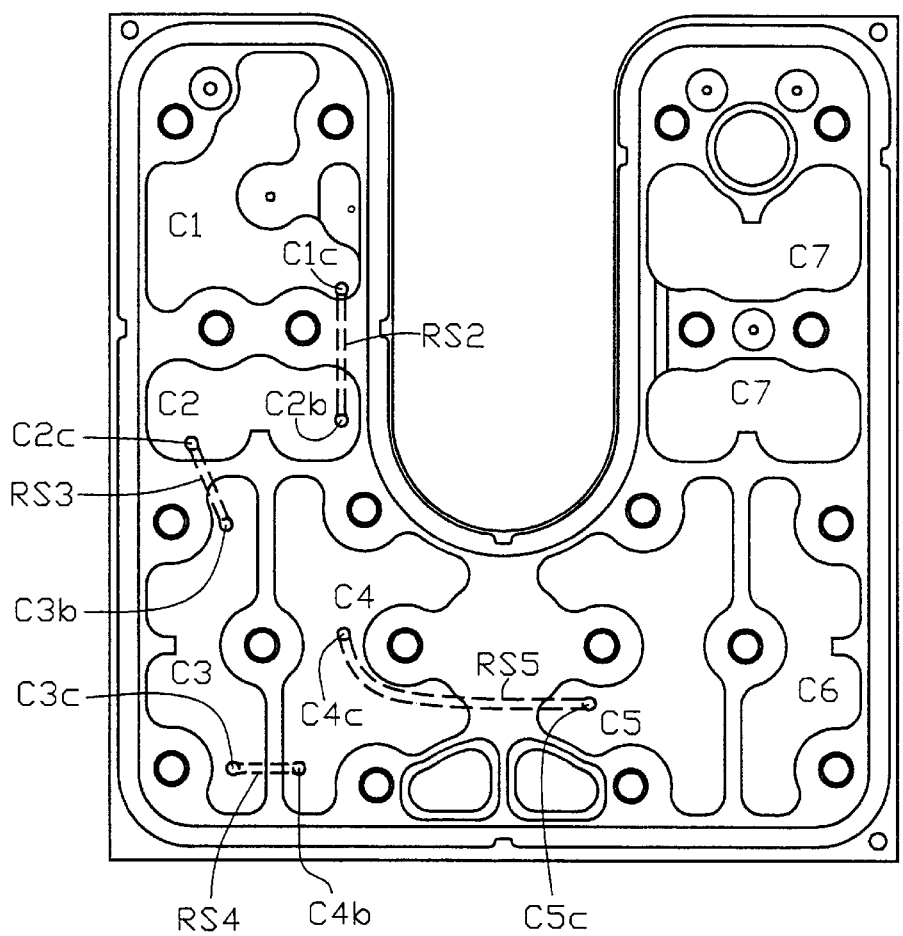
FIG. 6 illustrates further plate-shaped elements forming part of the sandwich device, said elements forming a shunt channel.

FIG. 6 is a top view in direction of the block, which is shown as solid lines, of the slits formed in the shunt channel foil 27 for providing the shunt channel 12 with its restrictions RS2–RS5 shown by means of dotted lines. Furthermore apertures in the separation foil 26 and the subjacent foils extending up to the cavities C1–C5 in the block 22 are illustrated by means of circles. The same reference numerals as in FIG. 2 have also been used in FIG. 6. The restriction RS2 is defined by a slit in the shunt channel foil 27, the subjacent separation foil 26 and the superjacent cover foil 28, said restriction further communicating with the cavities C1 and C2 via the apertures C1c and C2b, respectively. Correspondingly the slit forming the restriction RS3 in the shunt channel foil 27 communicates with the cavities C2 and C3 via the apertures C2c and C3b, the slit forming the restriction RS4 in the shunt channel foil 27 communicates with the cavities C3 and C4 via the apertures C3c and C4b, respectively, and the slit forming the restriction RS5 in the separation foil 26 communicates with the cavities C4 and C5 via the apertures C4c and C5c, respectively. It should be noted that some flow channels and through-going apertures defined by the elements of the sandwich device 21 have been omitted in FIGS. 5 and 6 in consideration of clarity. Moreover some flow channels and ancillary equipment have been omitted in FIGS. 1 and 2 for the same reason.

The invention has been described above with reference to a photoacoustic gas analyser comprising a sandwich device forming the acoustic filters. It should, however, be understood that the invention is not limited to the described embodiment or to photoacoustic gas analysers, but also comprises paramagnetic gas analysers within the scope of protection defined by the claims.

What is claimed is:

1. Gas analyser comprising a measuring chamber, a gas inlet channel for supplying gas to the measuring chamber, a gas outlet channel for removing gas from the measuring chamber, means for providing a predetermined gas volume flow rate through the measuring chamber, a device for affecting the gas in the measuring chamber with pulsating magnetic or electromagnetic energy of predetermined pulse rates so as to generate acoustic pressure fluctuations therein, and at least one microphone communicating with the measuring chamber for detecting said acoustic pressure fluctuations, the inlet channel and the outlet channel each comprising an acoustic filter in form of channel sections with reduced sectional area of flow so as to provide a predetermined flow resistance and a plurality of cavities of a predetermined volume connected therewith, characterised in that the gas analyser comprises at least one sandwich device formed of joined mutually parallel plate-like elements, the channel sections with reduced flow area of the inlet channel and/or the outlet channel being defined by at least two of said plate-like elements and the cavities also being defined by at least two of said plate-like elements, the connections between the respective channel and the respective cavities being provided as transverse apertures connecting the channel and the cavities, said transverse apertures extending transversely with respect to interface(s) between the plate-like elements constituting the sandwich device.

2. Gas analyser according to claim 1, characterised in that the acoustic filters of the inlet channel and outlet channel, respectively, are provided in the same sandwich device.

3. Gas analyser according to claim 1, characterised in that the channel or channels of the sandwich device is/are defined by a non-through-going groove in a first element and by an adjoining second element, in which the transverse apertures connecting the channel with the cavities are formed.

4. Gas analyser according to claim 3, characterised in that the transverse apertures are formed in the same element as the cavities, the cavities being defined by said element comprising the transverse apertures and the cavities together with a separate plate-like element.

5. Gas analyser according to claim 3, characterised in that the cavities are formed as recesses in a separate element abutting the element comprising the transverse apertures.

6. Gas analyser according to claim 1, characterised in that the channel or channels of the sandwich device is/are defined by a through-going slit in a first element and by adjoining further elements, one provided on either side of the first element, the transverse apertures connecting the channel with the cavities being formed in one of the further elements.

7. Gas analyser according to claim 6, characterised in that first element is formed of a metal foil having a thickness of between 0.05 and 0.5 mm, preferably 0.1 and 0.2 mm, the width of the slit exceeding the foil thickness, preferably by at least two to three times.

8. Gas analyser according to claim 6, characterised in that the transverse apertures are formed in the same element as the cavities, the cavities being defined by said element comprising the transverse apertures and the cavities together with a separate plate-like element.

9. Gas analyser according to claim 6, characterised in that the cavities are formed as recesses in a separate element abutting the element comprising the transverse apertures.

10. Gas analyser according to claim 1, characterised in that each of the cavities of the acoustic filter of the inlet channel communicates with the acoustic filter of the outlet channel via a shunt channel.

11. Gas analyser according to claim 10, characterised in that the shunt channel is provided partly by means of at least two plate-like elements of the sandwich device defining shunt channel sections, said elements preferably differing from the elements defining the inlet channel, the outlet channel and the cavities, respectively, and partly by means of transverse apertures connecting the shunt channel sections with the cavities in the acoustic filter of the inlet channel and with the acoustic filter of the outlet channel, respectively.

* * * * *